United States Patent [19]

Nakamura et al.

[11] Patent Number: 5,068,314
[45] Date of Patent: Nov. 26, 1991

[54] LIPOPOLYSACCHARIDE-BINDING POLYPEPTIDE

[75] Inventors: Takanori Nakamura, Asaka; Sadaaki Iwanaga; Motonori Ohno, both of Fukuoka; Kyosuke Miyazaki, Tokyo, all of Japan

[73] Assignee: Seikagaku Kogyo Co. Ltd., Tokyo, Japan

[21] Appl. No.: 348,487

[22] PCT Filed: Aug. 19, 1988

[86] PCT No.: PCT/JP88/00823
§ 371 Date: Aug. 19, 1989
§ 102(e) Date: Aug. 19, 1989

[87] PCT Pub. No.: WO89/01492
PCT Pub. Date: Feb. 23, 1989

[30] Foreign Application Priority Data

Aug. 21, 1987 [JP] Japan .................................. 206258

[51] Int. Cl.$^5$ .......................... A61K 37/02; C07K 7/08
[52] U.S. Cl. .................................................... 530/317
[58] Field of Search ....................... 514/13, 11; 530/317

[56] References Cited

U.S. PATENT DOCUMENTS 4,663,435  5/1987  Brady .................................. 530/317

OTHER PUBLICATIONS

Tokunaga, et al., "Tachyplesin a Class of Antimicrobial Peptide from the Hemocytes of the Horseshoe Crab (Tachypleus tridentatus), *J. Biol. Chem.*, v"ol. 263, No. 32, pp. 16709–16713, p. 1988.

Morita, et al., "Isolation and Biological Activities of Limulus Anticoagulant which Intera ts with Lipopolysaccharide", J. Biol. chem. 97, 1611–1620, 1985.

Shieh, et al., "Synthesis and properties of tachyplesin I, a lipolysaccharide-binding peptide, from Tachypleus tridentatus" Feb, 252, pp. 121–124.

Aketagawa et al., "Primary Structure of Limulus Anticoagulant Anti-lipopolysaccharide Factor", J. Biol. Chem. vol. 261, pp. 7357–7365, 1986.

*Primary Examiner*—Lester L. Lee
*Assistant Examiner*—S. G. Marshall
*Attorney, Agent, or Firm*—Jordan B. Bierman; Bierman and Muserlian

[57] ABSTRACT

This invention relates to a novel polypeptide represented by the formula:

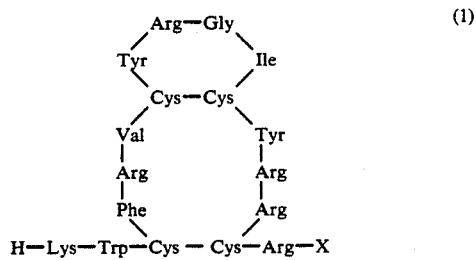

(wherein Lys represents lysine, Trp tryptophan, Cys cystine, Phe phenylalanine, Arg arginine, Val valine, Tyr tyrosine, Gly glycine, Ile isoleucine and X a hydroxyl group or an amino group), its analogue and a method for preparing the same.

The polypeptide exhibits strong affinity for lipolysaccharide, and is useful for removing endotoxin and as a therapeutic agent of bacterial infections.

2 Claims, 7 Drawing Sheets

LIPOPOLYSACCHARIDE-BINDING POLYPEPTIDE

TECHNICAL FIELD

This invention relates to a novel polypeptide and a method for preparing the same, more particularly to a novel polypeptide exhibiting strong affinity for lipopolysaccharide (endotoxin) and a method for preparing the same.

BACKGROUND ART

Endotoxin is also called an intracellular toxin, which term refers comprehensively to toxic substances existing in the cells of Gram-negative bacteria. The components of endotoxin are lipopolysaccharides (hereinafter called "LPS").

In the prior art, the pyrolysis method, the ultrafiltration method, and the affinity chromatographic method with polymixin B are known methods for removing endotoxin.

However, the pyrolysis method is a method which thermally decomposes LPS through a dry heat treatment at 250° C. or higher to remove LPS from glass vessels, etc. by decomposition. This pyrolysis method cannot be utilized for separating LPS from a substance which is unstable to heat. The ultrafiltration method is effective for separation of LPS from low molecular weight substances, but it is not applicable in principle for separation of endotoxin from high molecular weight substances. The affinity chromatographic method with polymixin B may be expected to be practically applied from the point of utilizing the affinity possessed by polymixin B for LPS, but use is limited because of the toxicity of polymixin B and thus, this method has not been presently practically applied.

Thus, there has not been found yet a practically effective method as the method for separating effectively and stably LPS from among high molecular weight physiologically active substances.

Accordingly, the present inventors have intensively studied in order to find novel substances exhibiting affinity for LPS. In the present invention, this substance is called as LPS-binding polypeptide (sometimes abbreviated to LBP). Consequently, they successfully extracted and isolated a novel polypeptide from horseshoe crab hemocyte, synthesized this polypeptide by the synthetic method such as solid phase peptide synthesis, and further found that said polypeptide exhibits strong affinity for LPS and has biological activities such as antibacterial activity and blastgenesis inhibition action, etc., thus accomplishing the present invention.

DISCLOSURE OF THE INVENTION

The present invention concerns a polypeptide represented by the formula:

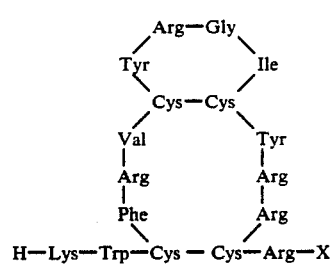

wherein Lys represents lysine, Trp tryptophan, Cys cystine, Phe phenylalanine, Arg arginine, Val valine, Tyr tyrosine, Gly glycine, Ile isoleucine and X a hydroxyl group or an amino group, its analogue and a method for preparing said polypeptide.

The compound of the present invention is a polypeptide comprising 17 amino acids, in which the carboxyl group of arginine which is the C-end amino acid is amidated under the extracted or isolated condition. Even when this polypeptide is converted to an acid by hydrolysis, the affinity for LPS remains high.

The polypeptide of the present invention can be extracted and isolated from horseshoe crab hemocyte of *Tachypleus tridentatus, Tachypleus gigas* or *Limulus Tachypleus gigas* as described below.

More specifically, the residue after hypotonic extraction of hemocyte of *Tachypleus tridentatus* is extracted under acidic condition, for example, in diluted mineral acid such as hydrochloric acid, nitric acid, sulfuric acid, etc; or in organic acid, for example, low aliphatic acid such as acetic acid, etc. The extract obtained is subjected to purification means such as gel filtration, chromatography, etc., whereby the polypeptide can be isolated.

The polypeptide of the present invention can be produced by the synthetic methods such as the peptide synthesis method, e.g. solid phase peptide synthesis method, liquid phase peptide synthesis method, etc.

More specifically, for example, in the solid phase synthetic method after the carboxyl group of N-protected arginine is bonded to an insoluble resin having amino groups, sometimes through a spacer having both carboxyl group and a functional group capable of bonding to a carboxyl group, the protected amino acids corresponding to the 16- to 1-positions of peptide sequence represented by the formula:

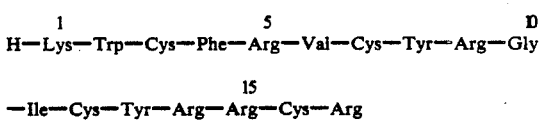

(wherein the symbols are the same as defined above) are bonded to the arginine which bound to the insoluble resin, in succession according to the solid phase peptide synthesis method to obtain the protected polypeptide, said insoluble resin and the protecting groups of these amino acids are eliminated to obtain a polypeptide represented by the formula (II):

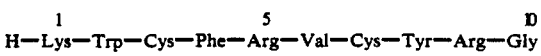

-continued

15
—Ile—Cys—Tyr—Arg—Arg—Cys—Arg—NH₂ wherein the symbols are the same as defined above and the cystines in the 3- and 16-positions and 7- and 12-positions are bonded each other through the respective mercapto groups to form disulfide bonds, whereby the polypeptide of the present invention can be produced.

Any resin which can be bonded to the carboxyl group of N-protected arginine (or in some cases the carboxyl group of the spacer bonded thereto) and which can thereafter be eliminated may be used as the insoluble resin having amino groups.

Examples of such insoluble resins may include aminomethyl resin {aminomethyl-poly(styrene-CO-divinylbenzene)}, benzhydrylamine resin, methylbenzhydrylamine resin, 4-(aminomethyl)phenoxymethyl resin, etc. By use of benzhydrylamine resin, methylbenzhydrylamine resin and 4-(aminomethyl)phenoxymethyl resin, an amide can be directly obtained by cleavage, but aminomethyl resin is preferred with respect to yield.

The spacer having both a carboxyl group, which exists in the above case, and a functional group capable of binding to a carboxyl group should be one which is capable of converting the carboxyl group of arginine to p-carboxymethylbenzyl ester, the choice of spacers is not particularly limited.

4-(t-butoxycarbonyl-G-tosyl-L-arginyloxymethyl)-phenylacetic acid comprising such a spacer bonded to the protected arginine can be prepared according to the method of J. P. Tam et al ("Synthesis" (1979), pp. 955 to 957).

A protected amino acid is an amino acid having a functional group protected with a protective group by a known method, and various protected amino acids are commercially available. In the case of synthesizing the polypeptide of the present invention, either one of the protective groups shown below should be preferably selected. First, the protective group for α-amino group of an amino acid is Boc (t-butyloxycarbonyl) or Fmoc (9-fluorenylmethyloxycarbonyl). The protective group for guanidino group of Arg may include Tos (tosyl), NO₂ (nitro), or Mtr (4-methoxy-2,3,6-trimethylbenzenesulfonyl). The protective group for a mercapto group of Cys may include Bzl (benzyl), M.Bzl (4-methoxybenzyl), 4-MeBzl (4-methylbenzyl), Acm (acetamidomethyl), Trt (trityl), Npys (3-nitropyridinsulphenyl), t-Bu (t-butyl), or t-BuS (t-butylmercapto). Among them, 4-MeBzl, Acm and Npys are preferred. The protective group for the hydroxyl group of Tyr may be Bzl, Cl₂Bzl (2,6-dichlorobenzyl), t-Bu, or this hydroxyl group may not be protected. The protective group for an ε-amino group of Lys may include Z (benzyloxycarbonyl), Cl.Z (2-chlorobenzyloxycarbonyl, Boc , or Nyps. It is necessary to select an adequate group for each protective group depending on the synthetic conditions of the peptide.

The protective group can be bound according to conventional condensation method such as the DCC (dicyclohexylcarbodiimide) method, the active ester method, the mixed or symmetric acid anhydride method, the carbonyldiimidazole method, the DCC-HOBt (1-hydroxybenzotriazole) method, the diphenylphosphorylazide method, etc., but the DCC method, the DCC-HOBt method and the symmetric acid anhydride method are preferred. These condensation reactions are generally carried out in an organic solvent such as dichloromethane, dimethylformamide, etc. or a solvent mixture thereof. Trifluoroacetic acid/dichloromethane, HCl/dioxane, piperidine/dimethylformamide, etc. are employed as the eliminating reagent for the protective group for an α-amino group. Suitably selection depends on which said protective group is being used. The extent of progress of the condensation reaction in the respective steps of synthesis is examined by the method of E. Kaiser et al [Anal. Biochem. 34, 595 (1970)] (the ninhydrin reaction method).

As described above, a protected peptide resin having a desired amino acid sequence can be obtained.

When an aminomethyl resin is used as the insoluble resin, for example, by treating the resin with ammonia in an appropriate solvent, said resin can be eliminated. Next, by treating the resin with hydrogen fluoride, the polypeptide having all the protective groups eliminated therefrom represented by the above formula (II) can be obtained. When benzhydrylamine resin, methylbenzhydrylamine resin or 4-(aminomethyl)phenoxymethyl resin is employed as the insoluble resin, said resin and the protective group can be eliminated at the same time by treating with hydrogen fluoride.

Next, by reducing preferably with 2-mercaptoethanol to ensure that the mercapto group of cystine is in the reduced form, oxidation treatment is performed to give the desired cyclic polypeptide of the formula (I) as the amide.

The oxidation treatment in this case can be carried out by use of the known method, and generally an oxidizing agent such as oxygen in the air, or ferricyanate (e.g. potassium ferricyanate) is used.

The polypeptide thus obtained can be purified by conventional means such as extraction, recrystallization, various chromatographies (gel filtratin, ion exchange, partition, adsorption, reverse phase), electrophoresis, countercurrent partition, etc., but the method by reverse phase high performance chromatography is the most effective.

BRIEF DESCRIPTION OF THE DRAWINGS

FIG. 10 is a diagram showing effect of polypeptide of the present invention against blastogenesis of human periphery lymphocyte due to LPS stimulation.

BEST MODES FOR PRACTICING THE INVENTION

The present invention is described in more detail by referring to Examples, but these Examples are not at all limitative of the present invention.

EXAMPLE 1

A. Extraction and Purification of the Polypeptide of the Present Invention

To about 50 g of the hemocyte of *Tachypleus tridentatus*, 150 ml of 20 mM tris-HCl/50mM NaCl pH 8.0 buffer was added, and the mixture was homogenized by a high speed homogenizer, Hiscotron (trade name; produced by Nippon Seimitsu Kogyo K.K.) for 3 minutes, and then centrifuged (8000 rpm, 30 min., 4° C.). For the thus separated precipitate, the above operation was repeated twice, and the soluble components in the hemocyte were sufficiently extracted to obtain the residue.

To the residue, added was 150 ml of 20 mM HCl, the mixture was homogenized by a high speed homogenizer for 3 minutes, and after centrifugation, a supernatant of acidic extract was obtained. By repeating this operation for a total of three times, about 400 ml of the whole amount of extract was obtained. The supernatant fraction was dried and concentrated by lyophilization.

The acidic extract, concentrated and dried, was redissolved in 20 mM HCl aq. soln. and then added into a Sephadex G-50 column (3.0×90.0 cm) (previously equilibrated with 20 mM HCl aq. soln.) to effect gel filtration. The eluted fractions inhibiting activation of C factor with LPS (one derived from *E. coli* 0111 B4 strain was used) (Horseshoe crab blood coagulating serine protease precursor; LPS-sensitive factor named by the present inventors, Nakamura et al., Eur. J. Biochem., 154, 511 (1986)) were collected, and the pH of the pooled fractions was adjusted to 6.0 with NaOH aq. soln.

The sample was applied to a CM-Sepharose CL-6B column previously equilibrated with 20 mM acetate buffer (pH 6.0) and elution was effected with a gradient of 20 mM acetate buffer (pH 6.0) containing 0 to 0.3M NaCl. The fractions inhibiting activation of C factor were collected to give the final purified preparation of the LPS-binding substance (novel polypeptide of the present invention). The yield was about 30 mg from about 50 g of hemocyte.

B. Purity Assay (1) SDS Polyacrylamide Gel Electrophoresis

Figure 1:
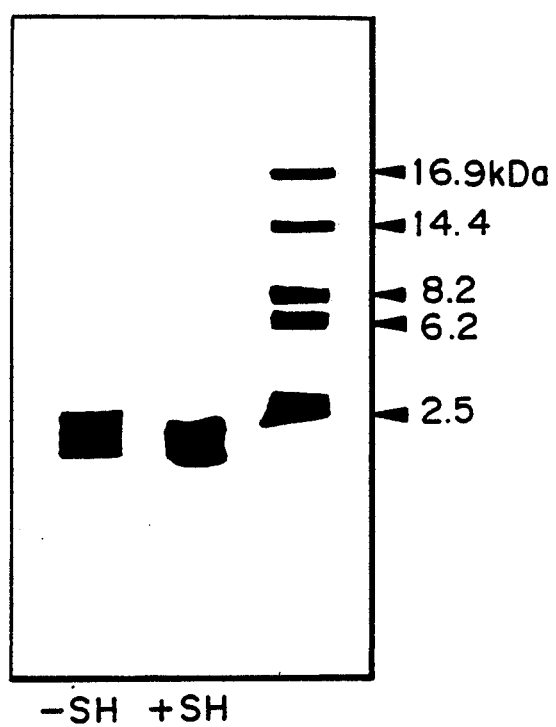
FIG. 1 is a chart showing the results of an SDS polyacrylamide gel electrophoresis of the polypeptide of the present invention.

LPS-binding polypeptide was subjected to 12% polyacrylamide gel electrophoresis containing 8M urea in the absence or presence of a reducing agent ($\beta$-mercaptoethanol) and stained with Coomassie Brilliant Blue R-250, whereby a single band of a molecular weight of 2,000 was exhibited in both cases. The results are shown in FIG. 1. In FIG. 1, the band on the left side shows the polypeptide in the absence of the reducing agent; the band in the center shows the polypeptide in the presence of the reducing agent; the band on the right side indicates the positions of myoglobin by a myoglobin standard protein marker [SDS PAGE Marker/III, Fluka AG (Switzerland)] (16.9 kDa), myoglobin I+II (14.4 kDa), myoglobin I (8.2 kDa), myoglobin II (6.2 kDa) and myoglobin III (2.5 kDa).

(2) Reverse Phase High Performance Liquid Chromatography

When the polypeptide of the present invention was analyzed by reverse phase high performance liquid chromatography (column was Cosmosil 5C$_{18}$P, peptide eluted with a gradient system of 0.1% trifluoroacetic acid/acetonitrile 0 to 98%), a single peak was exhibited.

C. Amino Acid Composition Value

The sample was hydrolyzed with 5.7M HCl aq. soln. at 110° C. for 24, 48 and 72 hours, and then analyzed by an Hitachi 835 amino acid analyzer. For half cystine, the sample was oxidized with performic acid and then hydrolyzed with 5.7M HCl aq. soln. at 110° C. for 24 hours. For tryptophan, the sample was hydrolyzed with 3M mercaptoethanesulfonic acid at 110° C. for 24 hours, and then analyzed by the amino acid analyzer. From the molecular weight obtained by SDS polyacrylamide gel electrophoresis, this peptide was found to be a single basic polypeptide constituting 17 amino acids. The results of analysis of amino acids are shown in Table.

TABLE 1

| Amino acid | Residue/molecule |
| --- | --- |
| Gly | 1.2 (1) |
| Cys/2 | 3.8 (4) |
| Val | 1.0 (1) |
| Ile | 0.9 (1) |
| Tyr | 1.8 (2) |
| Phe | 1.0 (1) |
| Lys | 0.9 (1) |
| Trp | 1.0 (1) |
| Arg | 4.8 (5) |
| Total | 17 |

D. Determination of Amino Acid Sequence and Identification of C-End Arginine Amide Amino acid sequence could be identified from the amino end up to the 15th residue (excluding half cystine) by use of about 23 $\mu$g of an intact preparation by means of Beckman 890 D sequencer. Also, by use of about 36 $\mu$g of a sample reductively alkylated {the polypeptide of the present invention subjected to S-pyridylethylation by the method of M. A. Hermodson, et al., Biochemistry, 12, 3146 (1973)}, identification could be made up to the 16th residue (including half cystine). The residual 17th amino acid residue (C-end residue) could be estimated to be arginine from amino acid analytical values. However, no C-end arginine could be detected even when an intact preparation, pyridylethylated preparation was used and digested with carboxypeptidase (hereinafter called "CPase") Y and B. Accordingly, the sample was once hydrolyzed with 30 mM HCl aq. soln. under mild conditions at 110° C. for 10 hours, and again treated with CPase B. As the result, about 0.5 mole of arginine was recognized to be liberated per mole of the polypeptide of the present invention, and the carboxyl group of the C-end was judged with great probability to be amidated. Because the theoretical molecular weight of the amide compound (calcd. MW=2,264) was completely coincident with the found value by mass analysis, the carboxyl group of the C-end arginine was confirmed to be amidated.

E. Identification of Disulfide Bond (S—S)

Four half cystines have been identified within the polypeptide of the present invention, and these were all found to be subjected to disulfide bonding from the comparative experiments of S-pyridylethylation in the presence or absence of a reducing agent (dithiothreitol). Accordingly, for identification of the positions of the disulfide bonds, an intact preparation was digested with trypsin under the conditions where no exchange reaction with disulfide bond occurs (under acidic conditions of pH 6.5), and the digested product was separated by reverse phase high performance liquid chromatography as described above (column was Cosmosil 5C$_{18}$P, peptide eluted with 0.1% trifluoroacetic acid/acetonitrile system). When the amino acid composition of the peptide obtained was examined, the 3rd and the 16th, the 7th and 12th from the amino end were found to be subjected to disulfide bonding.

F. LPS-Binding Activity of the Polypeptide of the Present Invention

The polypeptide of the present invention inhibited activation of C factor with 0.1 μg/ml of LPS (one derived from *E. coli* 0111 B4 strain was used) (represented as "C factor") 50% at 0.05 μM (0.12 μg/ml) and completely at 1 μM (2.3 μg/ml). Also, the polypeptide of the present invention was observed to form a polymer complex with LPS and to form a sedimentation line in the double diffusion test by use of 1% agarose gel.

Figure 2:
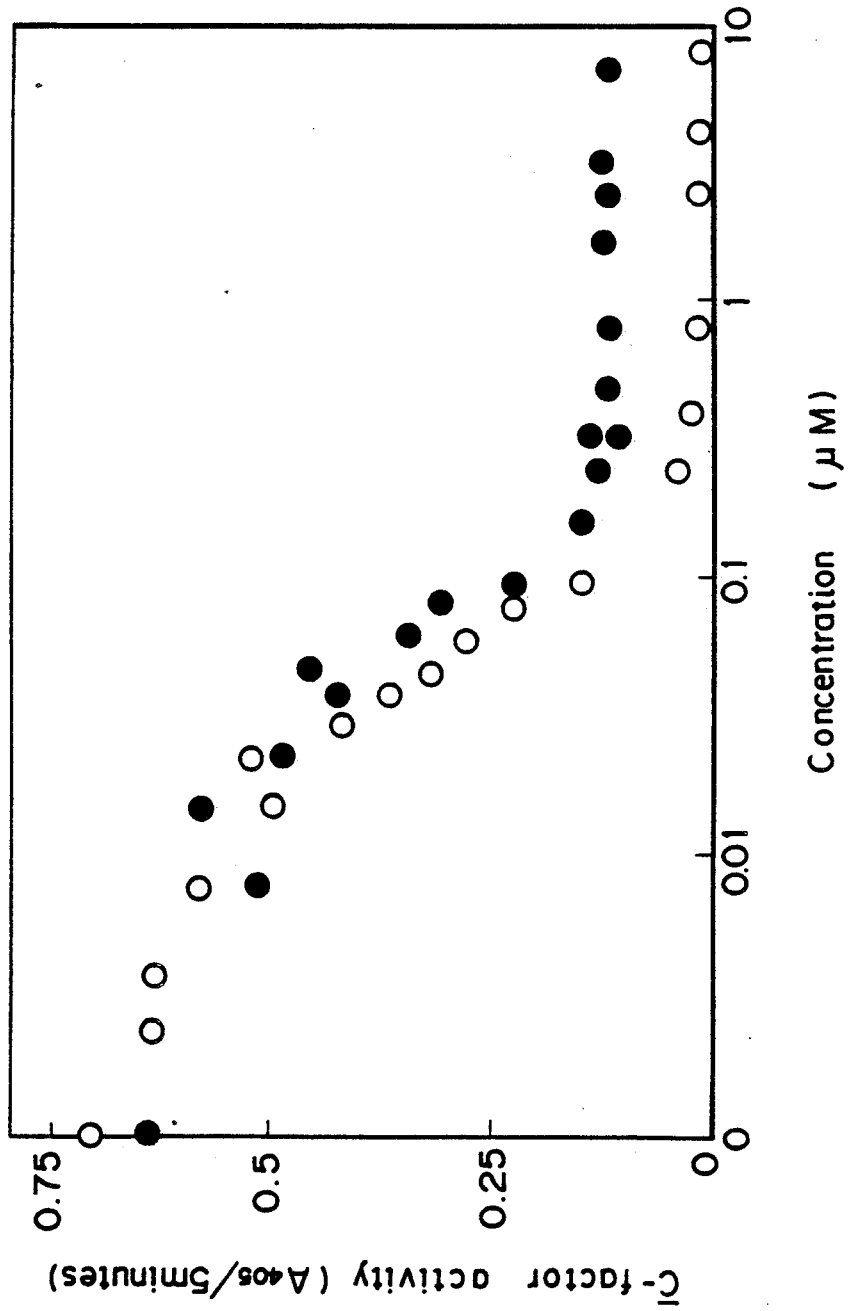
FIG. 2 and FIG. 3 are diagrams showing the test results regarding the inhibiting effect of the polypeptide of the present invention against activation of C factor by LPS.
Figure 3:
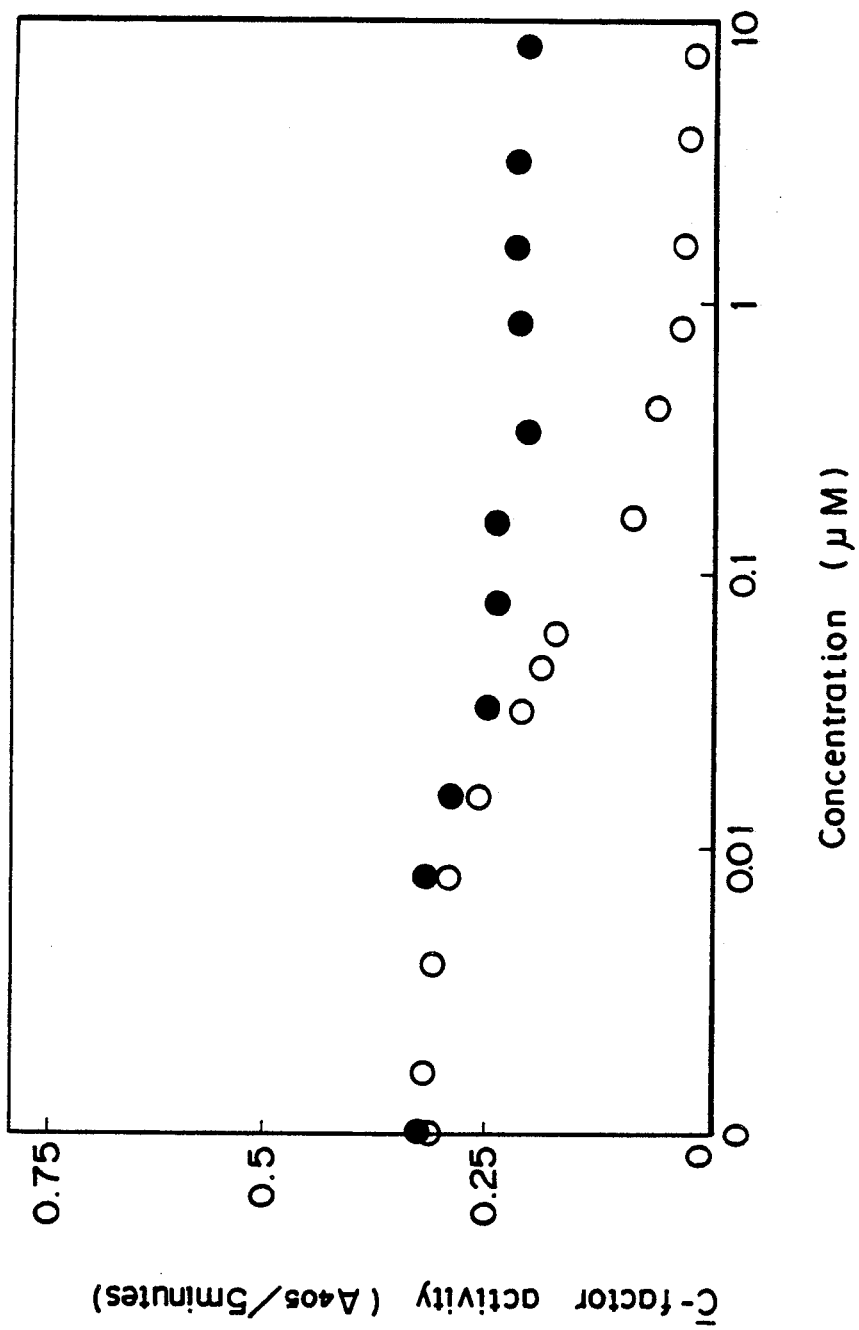

The test results for the inhibition effect of the polypeptide of the present invention against activation of C factor by LPS are shown in FIG. 2 and FIG. 3. FIG. 2 and FIG. 3 show the results in the absence or presence (1M) of sodium chloride, respectively. Polylisine, a high molecular weight basic substance exhibiting the property of binding electrically with LPS was used as a control. This property of binding electrically with LPS has been discovered by the present inventors. In FIG. 2 and FIG. 3, the marks (O) and (●) show the results of the polypeptide of the present invention and polylysine, respectively.

From these results, it can be understood that the novel polypeptide of the present invention does not merely exhibit electrical binding with LPS, but also strong affinity for LPS which is not influenced by the salt concentration.

G. Measurement of absorbance

Figure 4:
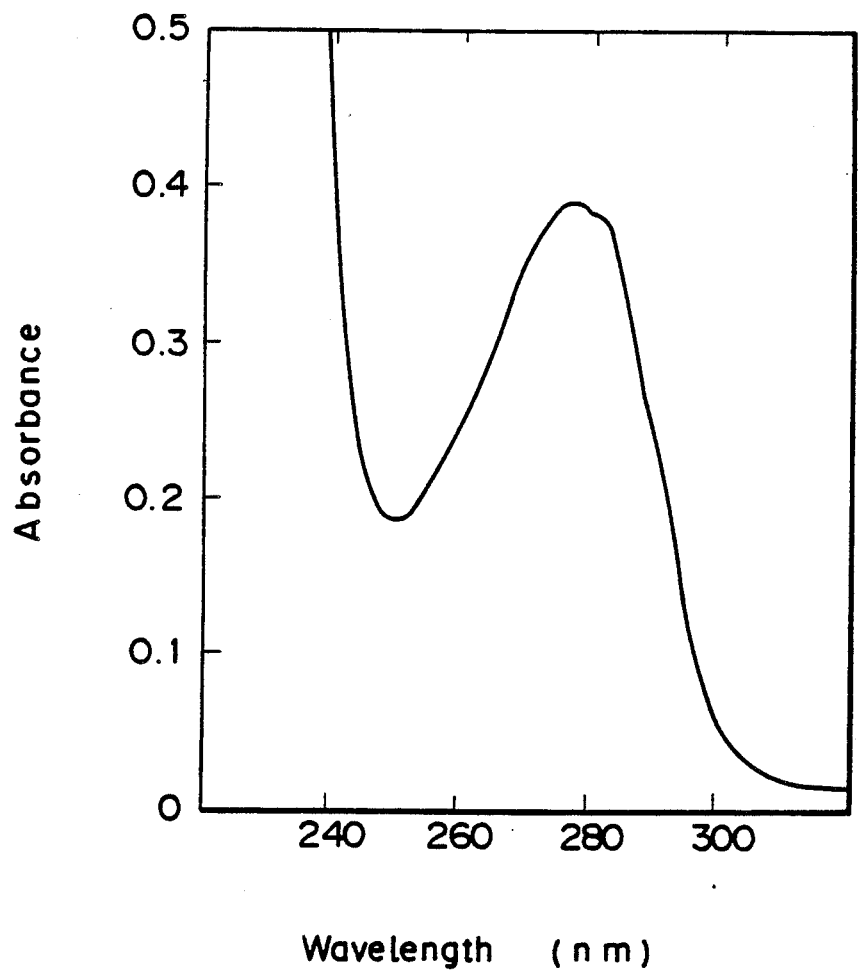
FIG. 4 is UV-ray absorption spectrum of the polypeptide of the present invention.

FIG. 4 shows the UV-ray absorption spectrum of an aqueous 99.2 μg/ml solution of the polypeptide of the present invention. It has the absorption peak at 276 nm. Since absorbance at 280 nm is 0.3842, the absorbance of 1% aqueous solution at 280 nm is calculated as 38.7.

EXAMPLE 2

A. Introduction of Arginine to Aminomethyl Resin (1) Synthesis of Phenacyl Ester of 4-(bromomethyl)-phenylacetic acid Into 75 ml of acetonitrile, 3.98 g (20 mmol) of α-bromoacetophenone and 3.49 g (60 mmol) of potassium fluoride were suspended at room temperature. 4.58 g (20 mmol) of 4-(bromomethyl)phenylacetic acid was divided into six equal parts, then these divided parts were added to the suspension while stirring at 30 minutes intervals, and the stirring was continued for further two hours. After completion of the reaction, insoluble products were filtrated off and solvents were distilled off from the filtrate. The residue was redissolved into ethylacetate and washed with aqueous saturated sodium hydrogen carbonate solution twice and subsequently washed with distilled water, citric acid and distilled water each once, followed by drying with sodium sulfate. Ethylacetate was distilled off and crystallization was conducted with petroleum ether to yield 5.5 g of objective product (melting point: 84° to 85° C.). The product was recrystallized to obtain 5.2 g of crystal with a melting point of 85° to 86° C. (yield: 75%).

(2) Synthesis of 4-(t-butoxycarbonyl-G-tosyl-L-arginyloxymethyl)phenylacetic acid A mixture of 4.71 g (11 mmol) of t-butoxycarbonyl-G-tosyl-L-arginine, 3.47 g (10 mmol) of phenacyl ester of 4-bromomethyl phenyl acetic acid, 1.28 g (22 mmol) of potassium fluoride, 0.8 ml (44 mmol) of water, 50 ml of acetonitrile and 10 ml of dimethylformamide was vigorously stirred at room temperature for 24 hours. The resulting insoluble product was naturally filtrated and the filtrate was concentrated to 15 to 20 ml by evaporation. After addition of 80 ml of ethylacetate thereto, the concentrate was washed with aqueous saturated sodium hydrogen carbonate solution twice, distilled water once, aqueous saturated citric acid solution twice and distilled water once, followed by drying with sodium sulfate. The solvent was distilled off and the residue was treated with petroleum ether to obtain phenacyl ester of 4-(t-butoxycarbonyl-G-tosyl-L-arginyloxymethyl)phenylacetic acid in semisolid state. It was dissolved into 105 ml of acetic acid, and then 19 ml of water and 13.1 g of zinc were added thereto, followed by vigorous stirring at room temperature for 5.5 hours. Zinc was filtrated off by use of a Hyflo Super Cel and ethylacetate and the filtrate was added with 400 ml of ethylacetate and 300 ml of water. An ethylacetate phase was separated and washed with water ten times. After drying with sodium sulfate, the solvent was distilled off and the residue was attrited in petroleum ether to yield 4.77 g of 4-(t-butoxycarbonyl-G-tosyl-L-arginyloxymethyl)phenylacetic acid. This substance was obtained as almost pure product at one spot by use of a thin-layer chromatography.

(3) Synthesis of 4-(T-Butoxycarbonyl-G-Tosyl-L-Arginyloxymethyl)Phenylacetamidomethyl resin 577 mg (1.0 mmol) of 4-(t-butoxycarbonyl-G-tosyl-L-arginyloxymethyl)phenylacetic acid, 2.00 g of aminomethyl resin (available from Peptide Laboratory K.K.; 1% crosslinked) and 206 mg (1.0 mmol) of DCC were subjected to a coupling reaction in dichloromethane by a conventional method. Revealed was coupling at 0.284 mmol per 1 g of a resin.

B. Introduction of 16-position cystine

An amount of 1.0 g {0.284 mmol Arg(Tos)/g resin} of 4-(t-butoxycarbonyl-G-tosyl-L-alginyloxymethyl)-phenylacetamidomethyl resin was washed with 25 ml of dichloromethane four times, each time for 1 minute, and filtrated. To the resulting resin, 25 ml of 30% trifluoroacetic acid solution (solvent: dichloromethane) was added and the mixture was stirred for 30 minutes, followed by elimination of a Boc group. The resulting resin was successively treated with 25 ml of each of the following solvents, with filtration following after each treatment.

Dichloromethane (once, 1 minute)
Dioxane (once, 1 minute)
Dichloromethane (once, 1 minute)
Dioxane (once, 1 minute)
Dichloromethane (twice, each 2 minutes)
10% Trimethylamine (dichloromethane solution) (once, 2 minutes; once, 5 minutes)
Dichloromethane (4 times, each 1 minute)

Subsequently, the above resin was stirred with 25 ml of dichloromethane and 3.5 equivalent amount of protected amino acid to total arginine amount, namely, 310 mg (0.994 mmlol) of Boc-Cys(4-MeBzl) for 1 minute. To the resulting mixture, 25 ml of dichloromethane solution containing 205 mg (0.994 mmol) of DCC was added and the mixture was stirred for 2 hours. The resulting resin was successively treated with 25 ml of each of the following solvents with filtration following after each treatment.

Dichloromethane (once, 1 minute)
Isopropanol (once, 1 minute)
Dichloromethane (once, 1 minute)
Isopropanol (once, 1 minute)

Dichloromethane (3 times, each 1 minute)

C. Introduction of 15- to 1-Position Amino Acid

To the resin previously obtained in the same manner as in B, the protected amino acid corresponding to the respective constituting amino acids on the 15- to 1-position of the polypeptide were coupled in succession. The protected amino acids used in the respective reaction steps are shown in Table 2. The amounts of the protected amino acids were all used in 3.5 equivalent amount to the total arginine amount. The coupling reaction of Boc-Arg(Tos) was conducted according to the DCC-HOBt method by using HOBt in twice the amount to DCC.

TABLE 2

| Position of amino acid | Protected amino acid |
|---|---|
| 15 | Boc—Arg(Tos) |
| 14 | Boc—Arg(Tos) |
| 13 | Boc—Tyr(Bzl) |
| 12 | Boc—Cys(4-MeBzl) |
| 11 | Boc—Ile |
| 10 | Boc—Gly |
| 9 | Boc—Arg(Tos) |
| 8 | Boc—Tyr(Bzl) |
| 7 | Boc—Cys(4-MeBzl) |
| 6 | Boc—Val |
| 5 | Boc—Arg(Tos) |
| 4 | Boc—Phe |
| 3 | Boc—Cys(4-MeBzl) |
| 2 | Boc—Trp |
| 1 | Boc—Lys(Cl.Z) |

After the introduction of the 1-positioned amino acid, the resinous peptide was recovered and collected in a glass filter by use of dichloromethane and then dried under reduced pressure to yield 1.781 g of dry resinous peptide.

D. Elimination of Resin

The dry resinous peptide obtained in C was treated with ammonia (no water) in methanol and dimethylformamide to eliminate the resin. The yield of the thus obtained protected polypeptide represented by the formula:

H -Lys(Cl.Z)-Trp-Cys(4-MeBzl)-Phe-Arg(Tos)
-Val-Cys(4-MeBzl)-Tyr(Bzl)-Arg(Tos)-Gly-Ile-
Cys(4-MeBzl)-Tyr(Bzl)-Arg(Tos)-Arg(Tos-Cys
(4-MeBzl)-Arg(Tos)—NH2 was 0.765 g (0.196 mmol). The molecular weight was 3,904.

E. Elimination of the Protective Group

The protected polypeptide obtained in D was treated with hydrogen fluoride in anisole in the presence of ethanedithiol to remove the protective group, and subsequently treated with anion exchange resin (Cl− type) and lyophilized to yield 470 mg (0.186 mmol) of polypeptide hydrochloride represented by the following formula:

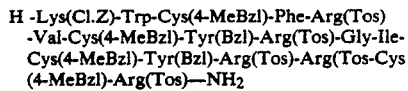
H-Lys-Trp-Cys-Phe-Arg-Val-Cys-Tyr-Arg-Gly
-Ile-Cys-Tyr-Arg-Arg-Cys-Arg- NH2.7 HCl The molecular weight was 2,523.

F. Cyclization of Polypeptide

An amount of 30 mg of the polypeptide hydrochloride obtained in E was left to stand in 0.1 M Tris-HCL (pH 8.5) containing 200-fold mol surplus 2-mercaptoethanol at room temperature for one night. Subsequently, it was treated with a Sephadex G-10 column equilibrated with 1% acetic acid to obtain the polypeptide-containing fraction. The fraction was diluted 10-fold (0.1 mg/ml) with water, adjusted to pH 8.5 with 0.5M NaOH and left to stand at room temperature for 30 hours, followed by lyophilization. Then it was treated with a Sephadex G-10 column equilibrated with 1% acetic acid to yield 8.5 mg of acidified polypeptide.

The thus obtained polypeptide was analyzed by reverse phase high performance liquid chromatography {the column was TSK-gel ODS-120T (0.46×25 cm), elution of the peptide was conducted with use of (A) 0.01M formic acid-triethylamine (pH 4.5) - (B) acetonitrile containing 20% of (A)}. As a result, a peak coincident with the natural polypeptide obtained in Example 1 was observed. Further, a mixture of them exhibited twice the peak and thus the identity thereof was recognized.

EXPERIMENTAL EXAMPLE 1

(Biological Activity of the Polypeptide According to the Ppresent Invention)

A Starting Material and Method (1) LPS

Purified LPSs whose S-type was Salmonella minnesota 1114 W, *E. colli* 0111:B4, *E. coli* 0113 and Re-type was Salmonella minnesota R595, *E. coli* J5 were used.

(2) LPS Sensitized Erythrocyte

To 1 ml of suspension containing mainly 2.5% human 0-type erythrocyte, 0.5 ml of LPS (1 mg/ml) was added and the mixture was shaken at 3.7° C. for 1 hour to mix, followed by washing with saline solution.

(3) Hemolysis Activity

A mixture of 50 μl of 0.5% LPS sensitized erythrocyte, 50 μl of 2-fold series diluted solution of 0.5% polypeptide of the present invention and 100 μl of Tris-HCl-buffered saline (pH 7.2) was maintained at 37° C. for 1 hour and thereafter 2.3 ml of physiologic saline was added thereto, followed by centrifugation with 2,500 rpm for 10 minutes. The amount of hemoglobin in the supernatant was determined by use of 412 μm absorption. Also, the hemolysis pattern on a micro plate was determined by use of a micro plate reader (Corona MPT-100: trade name) after maintaining a mixture of 50 μl of 0.5% LPS sensitized erythrocyte and 50 μl of 2-fold series diluted solution of 0.5% polypeptide at 37 ° C. for 1 hour.

(4) Antibacterial activity

Twenty μl of a 2-fold series diluted solution containing 0.5% polypeptide of the present invention and 20 μl of bacterium solution ($10^6$ to $10^7$/ml) were cultured onto 160 μl of a culture medium of Penassay or a synthetic medium of Jarvis. After 18 hours at 37° C., its turbidity was measured by use of a micro plate reader at 550 nm and also partial live bacteria number and inhibition circle were measured.

(5) Gel precipitin reaction

In a solution of 1% agarose (0.1% $NaN_3$ was added) dissolved in Tris-HCl-physiologic saline of pH 7.2, Beronall buffer of pH 8.6 and acetate buffer of pH 4.6, a sedimentation line was formed between LPS and the polypeptide of the present invention or anti-LPS factor {basic protein having MW of 11,600, consisting of amino acid 102 residue obtained from extract (lysate) of *Tachypleus tridentatus* hemocyte; hereinafter referred to "ALF"}. The line was dyed in amide black. The diluent used for the polypeptide of the present invention was 50 mM Tris HCl–0.15M NaCl (pH 7.2).

B. Results (1) Hemolysis Activity

The polypeptide of the present invention exhibited hemolysis at 2 to 3 μg/ml for erythrocyte sensitized by any LPS of Salmonella minnesota 1114 W, R595 and *E. coli* 0113 and, at high concentration, exhibited hemolysis with ease even at room temperature. Although hemolysis was inhibited by a free LPS which similarly inhibit ALF, hemolysis of non-sensitized erythrocyte was also observed in an amount of 3.13 μg/ml or more. Generally, hemolysis activity of the polypeptide of the present invention was weaker than that of ALF.

(2) Antibacterial Activity

The polypeptide of the present invention exhibited antibacterial activity for any of *Salmonella typhimurium* LT 2(S), 1102(Re), Salmonella minnesota 1114 W(S) and R 595(Re). A minimum antibacterial dose was 3.13 μg/ml for LT2 and 1.56 μg/ml for 1102. Moreover, it exhibited antibacterial activity even to Gram positive bacteria such as Staphylococcus aureus. On an agar containing bacteria, the inhibition circle was formed depending on the concentration. The antibacterial activity of the polypeptide of the present invention was genarally stronger than that of ALF.

(3) Gel Precipitin Reaction

The polypeptide of the present invention exhibited sharp sedimentation lines in the gel precipitin reaction for any LPS of Salmonella minnesota 1114 W, R595, *E. coli* 0111:B4, 0113 and J5. Sedimentation lines for heterogeneous LPS were fused with each other.

From the above, the polypeptide of the present invention exhibits strong affinity for LPS and is useful as a means for removing endotoxin and as a therapeutic agent for treating infections due to microorganisms.

Experiment 2

(Inhibition Action of the Polypeptide of the Present Invention Against Blastgenesis of Lymphocyte by LPS)

A. Material and Method

Spleen cells (SC) of C57BL male mouse (5 weeks age) was collected by use of Ficoll-Hypaque gravity centrifugation and suspended in RPMI-1640 culture medium (no serum or added with BSA, FCS). The resulting culture medium was adjusted to $3 \times 10^6$ cell/ml and 100 μl was distributed into each of the 96-holes of a microtiter plate. 10 μl each of 0.4, 4, 40 and 400 μg/ml polypeptide of the present invention (LBP), finally then 80 μl of the culture medium, and finally 10 μl of 400 μg/ml LPS were added to the distibuted culture medium, followed by incubation in 5% $CO_2$ incubator for 72 hours. $^3$H-thymidine ($^3$H-TdR) was added thereto in an amount of 1 μci/10 μl 18 hours before completion of the incubation. The amount of $^3$H-TdR collected after peeling off of cells by use of cell harvester was measured by use of a liquid scintillation counter to discover the index of cell multiplication.

Cell multiplication was observed by using a microscope to take an invert image microphotograph.

B. Results

Figure 5:
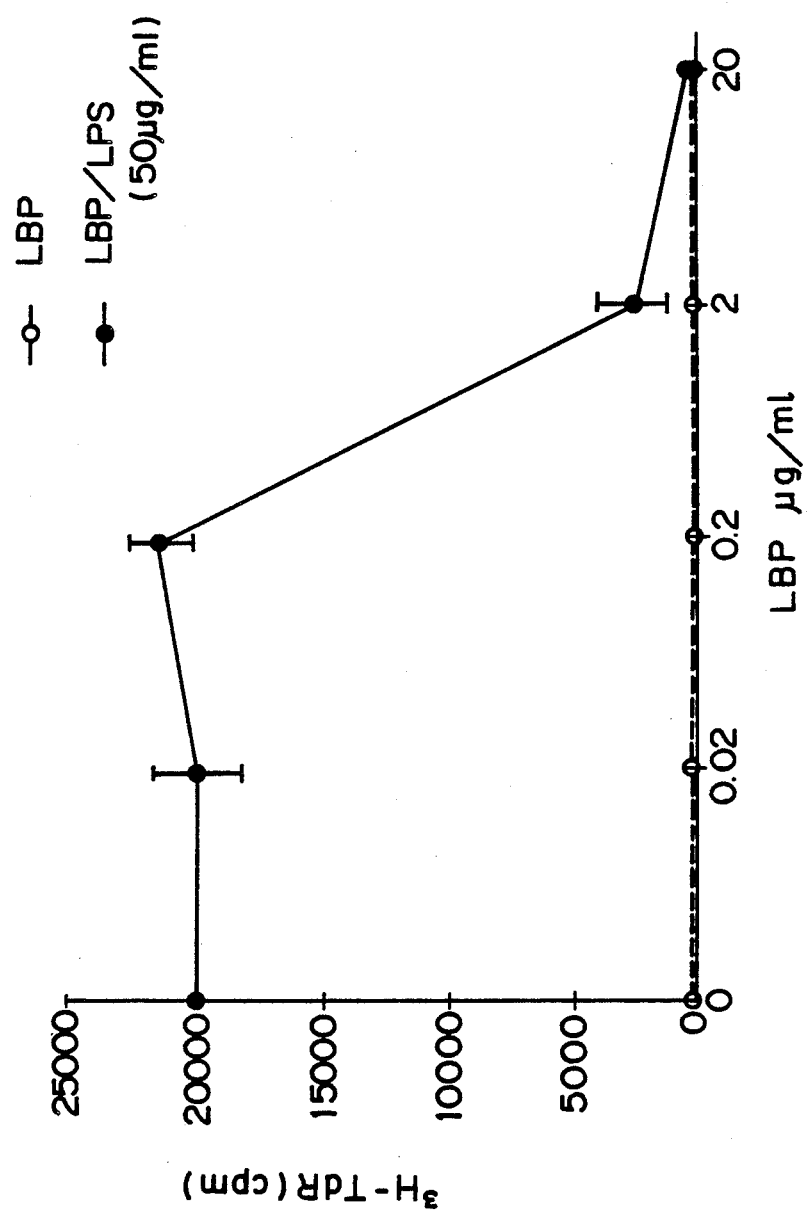
FIG. 5 shows effect of the polypeptide of the present invention against blastogenesis of lymphocyte of mouse due to LPS stimulation.
Figure 6:
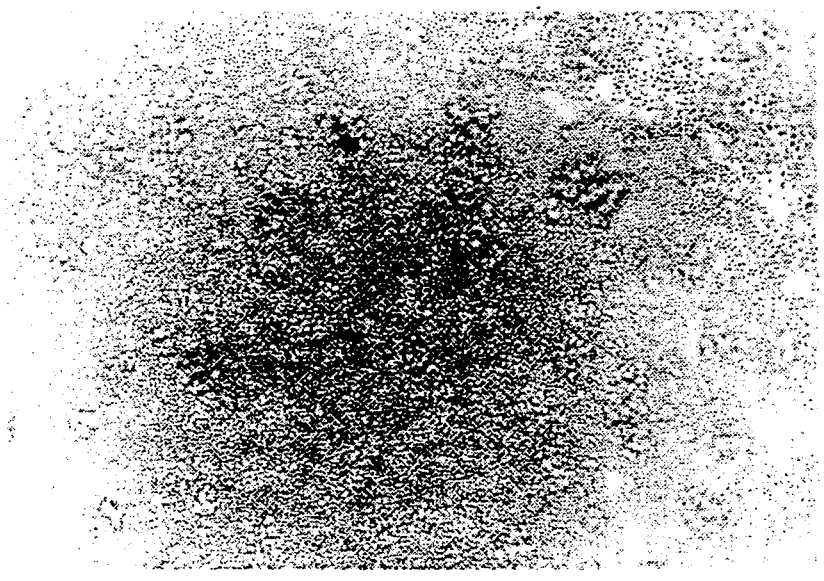
FIG. 6 is a microphotograph showing blastogenesis of lymphocyte when 50 μg/ml LPS is added.
Figure 7:
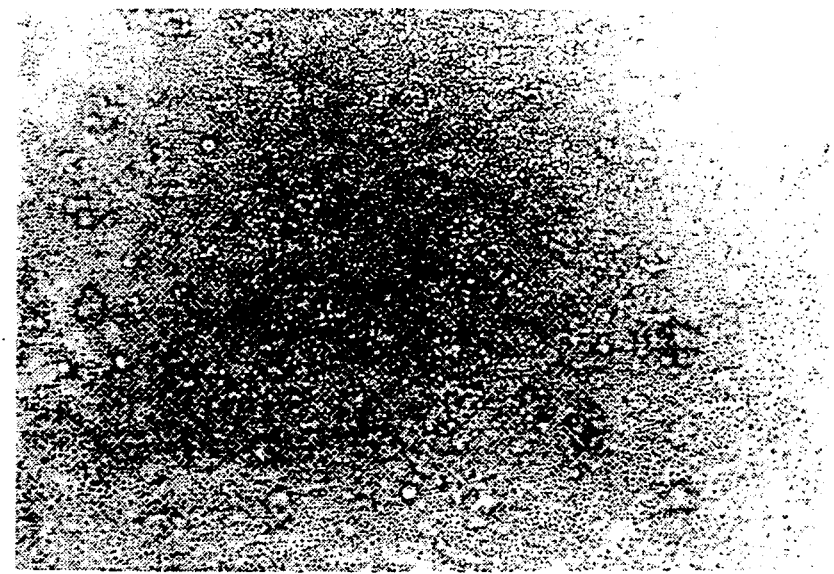
FIG. 7, FIG. 8 and FIG. 9 are each microphotographs to which, after 0.2, 2 and 20 μg/ml polypeptide of the present invention are added respectively, 50 μg/ml LPS is added respectively.
Figure 8:
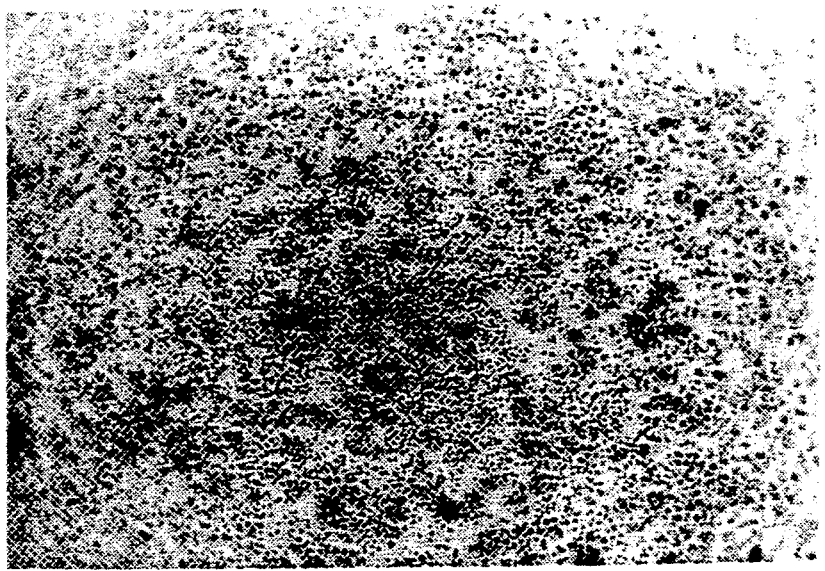
Figure 9:

FIG. 5 shows inhibition action of LBP against blastogenesis of mouse lienis SC (cell multiplication reaction) in the presence of LPS. As will be clear from the drawing, 2 μg/ml and 20 μg/ml of LBP inhibit 90% or more of blastogenesis of lymphocyte. Moreover, by observing by use of a microscope producing an inverted image, magnification and colonization (blastogenesis) were apparently revealed after adding 50 μg/ml LPS and subsequently incubating for three days (FIG. 6). Although few change were revealed in the case where LPS was added after addition of 0.2 μg/ml LBP (FIG. 7), magnification and colonization were hardly revealed in the case of using 2 μg/ml LBP and 20 μg/ml LBP to exhibit inhibition action against blastogenesis by LPS (FIG. 8 and FIG. 9).

EXPERIMENT 3

(Inhibition Action of the Polypeptide of the Present Invention Against Blastogenesis of Lymphocyte by LPS)

A. Material and Method

Peripheral blood mononuclear cells (PBNC) of healthy human (male, 30 years age) were collected by use of Ficoll-Hypaque gravity centrifugation and suspended in RPMI-1640 culture medium (no serum or added with BSA, FCS). The resulting culture medium was adjusted to $2 \times 10^6$ cell/ml and 100 μl was distributed into each of the 96-holes of a microtiter plate. 10 μl of 200 μg/ml LBP, then 80 μl of the culture medium, and finally 10 μl of 400 μg/ml LPS were added to the distributed culture medium, followed by incubation in 5% $CO_2$ incubator for 72 hours. $^3$H-thymidine ($^3$H-TdR) was added thereto in an amount of 1 μci/10 μl 18 hours before completion of the incubation. The amount of $^3$H-TdR collected after peeling of cells by use of cell harvester was measured by use of a liquid scintillation counter to discover the index of cell multiplication.

B. Results FIG. 10 shows inhibition action of LBP against blasto-genesis of PBMC (cell multiplication reaction) in the presence of LPS. As will be clear from the drawing, 10 μg/ml of LBP inhibit approximately 100% of blastogenesis of lymphocyte by 50 μg/ml LPS.

From the above results, it is recognized that LBP can almost completely inhibit blastogenesis of lymphocyte of human and mouse due to LPS stimulation in an amount of 1/25 to 1/5 based on the amount of LPS.

The binding activity between LBP and LPS was measured by using the C factor activity inhibition as an index to show about 20 times amount of LPS amount. Accordingly, the inhibition action of LBP against blastogenesis of lymphocyte is considered to be revealed by binding ability with LPS, and antagonism with a LPS receptor existing on cell membrane of lymphocyte (T cell, B cell) and monocyte or cell membrane's modification due to positive charge of LBP.

A LPS receptor exists in various cells, other than the above cells, macrophage, neutrophile, erythrocyte, thrombocyte, blood vessel, endothelial cell, hepatocyte, etc., and it is estimated that stimulation of LPS causes various immune reactions such as B cell blastogenesis, ajuvant action, polyclonal B cell activation, interleukin production, interferon production, TNF production, etc.; inflammation such as prostaglandin production, active oxygen production, complement activation, etc.

It is expected that LBP can almost completely inhibit directly or indirectly the above immune reactions and inflammation caused by LPS in 1/25 to 1/5 amount to the LPS amount. Accordingly, the polypeptide of the present invention can be sufficiently expected to be effective against the following diseases: infections such as superior tracheobronchial infection, unitary infection, etc., dermal disease such as bedsore, burn or scald, etc., colitis such as ulcerative colitis, clone disease ,etc., hepatopathy such as cirrhosis, hepatic insufficiency, etc., and postoperative complications in surgery.

POSSIBILITY OF APPLICATION IN INDUSTRY

The polypeptide of this invention exhibits strong affinity for lipopolysaccharide, and is useful for removing endotoxin and as a therapeutic agent of bacterial infections.

We claim:

1. A polypeptide represented by the formula:

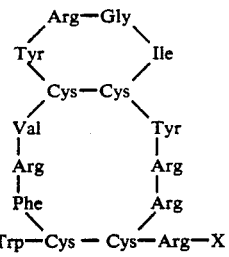

(1)

wherein Lys represents lysine, Trp tryptophan, Cys cystine, Phe phenylalanine, Arg arginine, Val valine, Tyr tyrosine, Gly glycine, Ile isoleucine and X a hydroxyl group or an amino group.

2. A polypeptide represented by the formula:

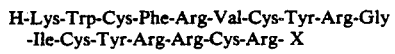

wherein Lys represents lysine, Trp tryptophan, Cys cystine, Phe phenylalanine, Arg arginine, Val valine, Tyr tyrosine, Gly glycine, Ile isoleucine and X a hydroxyl group or an amino group.

* * * * *

UNITED STATES PATENT AND TRADEMARK OFFICE
CERTIFICATE OF CORRECTION

PATENT NO. : 5,068,314

DATED : November 26, 1991

INVENTOR(S) : T. Nakamura, et al

It is certified that error appears in the above-identified patent and that said Letters Patent is hereby corrected as shown below:

In the abstract line 5, column 2, line 14, column 4, line 25, column 6, lines 3, 29 to 30 and 36 and column 14 lines 14 and 22 correct "cysteline"

Column 3 line 6 and column 6 line 56 correct "cysteines"

Column 2 lines 26 and 27 change "Tachypleus gigas" to --polyphemus --

Signed and Sealed this

Twenty-second Day of June, 1993

MICHAEL K. KIRK

*Attesting Officer*     Acting Commissioner of Patents and Trademarks

UNITED STATES PATENT AND TRADEMARK OFFICE
CERTIFICATE OF CORRECTION

PATENT NO. : 5,068,314
DATED : November 26, 1991
INVENTOR(S) : Nakamura, et al

It is certified that error appears in the above-identified patent and that said Letters Patent is hereby corrected as shown below:

In the Abstract line 5, Column 2, line 14, Column 4, line 25, Column 8, line 35, Column 14, lines 14 and 22, correct "cysteine"

Column 2, lines 26 and 27, change "Tachypleus gigas or Limulus Tachypleus gigas" to --or Tachypleus gigas--

Column 3, line 6, correct "cysteines"

Signed and Sealed this

Twenty-second Day of March, 1994

Attest:

BRUCE LEHMAN

Attesting Officer    Commissioner of Patents and Trademarks